United States Patent
Preussner

(10) Patent No.: US 7,001,428 B2
(45) Date of Patent: Feb. 21, 2006

(54) STIFFENABLE CAPSULE CLAMPING RING

(76) Inventor: Paul Rolf Preussner, Am Linsenberg 18, Mainz (DE) 55131

( * ) Notice: Subject to any disclaimer, the term of this patent is extended or adjusted under 35 U.S.C. 154(b) by 0 days.

(21) Appl. No.: 10/415,865

(22) PCT Filed: Aug. 31, 2002

(86) PCT No.: PCT/EP02/09755

§ 371 (c)(1),
(2), (4) Date: May 2, 2003

(87) PCT Pub. No.: WO03/022182

PCT Pub. Date: Mar. 20, 2003

(65) Prior Publication Data

US 2004/0034416 A1    Feb. 19, 2004

(30) Foreign Application Priority Data

Sep. 6, 2001    (DE) ............................... 101 43 634

(51) Int. Cl.
*A61F 2/14*    (2006.01)
*A61F 2/16*    (2006.01)

(52) U.S. Cl. ..................................... 623/4.1; 623/6.39
(58) Field of Classification Search .................. 623/4.1, 623/5.12, 6.37, 6.38–6.55, 6.6, 6.22, 5.16, 623/6.17, 6.11, 6.12
See application file for complete search history.

(56) References Cited

U.S. PATENT DOCUMENTS

| | | | | |
|---|---|---|---|---|
| 3,979,780 A | * | 9/1976 | Boniuk ....................... | 623/6.14 |
| 4,053,953 A | * | 10/1977 | Flom et al. ................. | 623/6.38 |
| 4,575,373 A | | 3/1986 | Johnson | |
| 4,786,445 A | * | 11/1988 | Portnoy et al. ............. | 264/1.37 |
| 5,252,262 A | * | 10/1993 | Patel ......................... | 264/1.26 |
| 5,725,575 A | | 3/1998 | O'Donnell, Jr. | |
| 5,855,604 A | * | 1/1999 | Lee ............................ | 623/5.12 |
| 6,197,056 B1 | * | 3/2001 | Schachar .................... | 623/4.1 |
| 6,319,282 B1 | * | 11/2001 | Nishi ......................... | 623/6.39 |
| 6,428,572 B1 | * | 8/2002 | Nagai ......................... | 623/4.1 |
| 6,543,453 B1 | * | 4/2003 | Klima et al. ................ | 128/898 |

FOREIGN PATENT DOCUMENTS

| | | |
|---|---|---|
| DE | 4030899 | 4/1992 |
| DE | 19530465 | 1/1997 |
| DE | 19637962 | 5/1998 |
| DE | 19904441 | 9/2000 |
| DE | 19951148 | 4/2001 |
| WO | 9749354 | 12/1997 |

OTHER PUBLICATIONS

U. S. Appl. No. 10/004,708, filed Jun. 21, 2001, Hidenobu Nagai.

* cited by examiner

*Primary Examiner*—Corrine McDermott
*Assistant Examiner*—Cheryl Miller
(74) *Attorney, Agent, or Firm*—Ostrolenk, Faber, Gerb & Soffen, LLP

(57) ABSTRACT

A capsule clamping ring for implantation in the emptied capsule of the human crystalline lens which can permanently counteract a shrinkage of the capsule thanks to the fact that it can be stiffened after implantation. The open ring—as required for implantation—is designed in such a manner that it can be welded inside the eye. For this purpose, the open ends must touch, the area of contact must be visible through the pupillary opening and thus accessible for the laser, and the colour of the material and the surface geometry must be designed in such a manner that, when irradiated with a laser, locally circumscribed, merging melting zones can form.

15 Claims, No Drawings

STIFFENABLE CAPSULE CLAMPING RING

TECHNICAL FIELD

The invention is an implant which can be inserted into the capsule sac of the human eye in the course of an operation on the opaque crystalline lens.

STATE OF THE ART

In an operation on an opaque crystalline lens (grey cataract), in general nowadays the capsule sac of the lens is opened, the opaque interior of the lens is drawn off, and then an artificial lens is inserted into the capsule sac. In the course of the following weeks and months, an individually more or less marked shrinkage of the capsule sac takes place. This is undesirable, especially if the intraocular lens is to be changed at some later time (e.g. in the case of children), or if as wide an expansion of the capsule sac as possible permanently is desired for other reasons, as is known for instance in the case of toric intraocular lenses or in the case of an accommodative implant, such as e.g. from DE19904441. In order to ensure an expansion of the capsule sac, elastic, open rings, with a break in their ring shape, so-called capsule clamping rings in keeping with the state of the art, are well known. They can, it is true, reduce the shrinking process of the capsule sac, but not completely prevent it. The reason for this is that, on the one hand, the capsule clamping ring may not be too stiff, in order that it can still be inserted into the very fragile capsule without injuring it, but, on the other hand, precisely because of that it cannot offer sufficient force to counter the shrinking process. Mechanical elements, with which one could bring about a stiffening of the ring after insertion into the capsule sac, such as pins, rivets, catches (e.g. DE4030899, DE19951148, US2001/0004708, DE19637962), etc. are little suited intraoperatively on account of their smallness, the sensitiveness of the capsule sac and the additional time required during the operation to handle them.

The object of this present invention is to make a capsule clamping ring available which can be stiffened in a simple manner after its insertion into the capsule sac.

BRIEF DESCRIPTION OF THE INVENTION

The object is solved by the invention in accordance with the distinguishing features of claim 1. The capsule clamping ring is executed in such a manner that its open ends touch after implantation in an overlapping area without any space in between. The overlapping area must lie within the pupillary opening, that is to be dilated if necessary, so that it is visible from outside.

In this contact area at least, the material is dyed in such a manner that it absorbs the light of a CW laser for the most part for the wavelength for which the refractive media of the eye are transparent. With the help of such a laser, the ends can then be welded inside the capsule sac in accordance with the well-known principles of welding technology, if the parts lying on top of one another are suitable from their surface form to form merging melting zones.

PREFERRED EXECUTION AND EXECUTION ALTERNATIVES

In its preferred execution, the capsule clamping ring is made of polymethylmetacrylate as this material has proved itself for capsule clamping rings on account of its mechanical properties and its biocompatibility, and because it can be easily welded.

The outside diameter of the rings is typically about 12–14 mm so that it can resiliently expand the capsule that has an equatorial diameter of ca. 9–11 mm. The thickness of the material of the ring is about 0.2 mm. The ends of the ring are widened out flag-like ca. 2.5 mm inwards in such a manner that, after implantation, a partial overlapping of these flags comes about whereby, as a result of the usual implantation process, the end inserted later into the eye, hereinafter called the "second end" lies in front of the one inserted first. "Before" and "in front" mean, here and hereinafter, in the direction of the cornea of the eye, i.e. parallel to the optical axis; "inside" in the direction of the ring or eye centre, i.e. vertical to the optical axis. The flags are designed in such a manner at the areas touching that they absorb in green, because most of the lasers used in ophthalmology work in this wavelength range (511 mm or 532 mm respectively). In the case of the second flag end at least, the dyeing must not go right through, but only be present on the rear side as the laser light would not otherwise be absorbed at the required point. The flag-like widening inwards is also necessary because the capsule clamping ring would otherwise be concealed by the iris after implantation, and thus no longer accessible for the laser light.

In another version, the flag of the second end contains small, conical drill holes, whereby the end of the drill hole with the smaller diameter rests against the other flag after implantation. The welding then takes place inside the drill holes. The advantage of this version is that the entire material can absorb uniformly, i.e. can be dyed homogeneously.

In a further version, the second flag projects less far inwards than the first one does. The second flag is bevelled towards the first one. This makes for good welding in the area of the bevel. In this version the entire material can also be dyed homogeneously.

What is claimed:

1. A capsule clamping ring for implantation into a capsule sac of a human crystalline lens of an eye, the capsule clamping ring comprising:
an unclosed ring body having first and second end regions, the ring body being structured such that the first and second end regions of the ring body contact one another at an optically accessible area of contact when the ring body is implanted into the capsule sac of the human crystalline lens, the first and second end regions of the ring body being colored to permit light of a CW laser to be absorbed by the first and second end regions at the contact area to weld the first and second end regions together after the ring body is implanted into the capsule sac of the human crystalline lens; the ring body has a center, the first and second end regions of the ring body are flag-shaped in a direction toward the center of the ring body, the flag-shaped end regions of the ring body have respective front sides adapted to face a cornea of the eye and have respective rear sides adapted to face away from the cornea of the eye, the first flag-shaped end region of the ring body overlaps the second flag-shaped end region of the ring body at the contact area such that the rear side of the first flag-shaped end region faces the front side of the second flag-shaped end region at the contact area when the ring body is implanted into the capsule sac of the human crystalline lens.

2. The capsule clamping ring of claim 1, wherein the first and second end regions of the ring body do not contact one another before the ring body is implanted into the capsule sac of the human crystalline lens.

3. The capsule clamping ring of claim 1, wherein the first and second end regions of the ring body are colored to absorb green light.

4. The capsule clamping ring of claim 3, wherein the first and second end regions of the ring body are colored to absorb wavelengths of the green light between 511 mm and 532 mm.

5. The capsule clamping ring of claim 1, wherein the rear side of the first flag-shaped end region and at least the front side of the second flag-shaped end region are colored to permit the light of the CW laser to be absorbed by the first and second end regions of the ring body at the contact area to weld the first and second end regions together and the remainder of the first flag shaped end region is transparent.

6. The capsule clamping ring of claim 1, wherein the first flag-shaped end region includes crater-shaped holes tapering toward the second flag-shaped end region at the contact area, such that the light of the CW laser is absorbable by the second flag-shaped end region in an area of the crater-shaped holes to weld the first and second end regions together.

7. The capsule clamping ring of claim 1, wherein the second flag-shaped end region protrudes further towards the center of the ring body than the first flag-shaped end region, and the first flag-shaped end region of the ring body is beveled towards the second flag-shaped end region of the ring body at the contact area.

8. A method of inserting a capsule clamping ring into a capsule sac of a human crystalline lens of an eye, the method comprising:
   inserting an unclosed ring body having first and second end regions into the capsule sac of the human crystalline lens, such that the first and second end regions of the ring body contact one another at an optically accessible area of contact when the ring body is inserted into the capsule sac of the human crystalline lens; and
   welding the first and second end regions of the ring body together using light.

9. The method of claim 8, wherein the welding of the first and second end regions of the ring body is performed using light of a CW laser.

10. The method of claim 9, wherein the first and second end regions of the ring body are colored to permit the light of the CW laser to be absorbed by the first and second end regions during the welding step.

11. The method of claim 9, wherein the first and second end regions of the ring body do not contact one another before the ring body is inserted into the capsule sac of the human crystalline lens.

12. The method of claim 9, wherein the ring body has a center, the first and second end regions of the ring body are flag-shaped in a direction toward the center of the ring body, the method further comprising:
   positioning the flag-shaped end regions of the ring body such that respective front sides thereof face a cornea of the eye and respective rear sides thereof face away from the cornea of the eye; and
   overlapping the first flag-shaped end region of the ring body over the second flag-shaped end region of the ring body at the contact area, such that the rear side of the first flag-shaped end region faces the front side of the second flag-shaped end region at the contact area when the ring body is inserted into the capsule sac of the human crystalline lens.

13. The method method of claim 12, wherein the rear side of the first flag-shaped end region and at least the front side of the second flag-shaped end region are colored to permit the light of the CW laser to be absorbed by the first and second end regions at the contact area during the welding step and the remainder of the first flag shaped end region is transparent.

14. The method of claim 12, wherein the first flag-shaped end region includes crater-shaped holes tapering toward the second flag-shaped end region at the contact area, such that the light of the CW laser is absorbable by the second flag-shaped end in an area of the crater-shaped holes during the welding step.

15. The method of claim 12, wherein the second flag-shaped end region protrudes further towards the center of the ring body than the first flag-shaped end region, and the first flag-shaped end region of the ring body is beveled towards the second flag-shaped end region of the ring body at the contact area.

* * * * *